US012090336B2

(12) United States Patent
Kerns et al.

(10) Patent No.: US 12,090,336 B2
(45) Date of Patent: Sep. 17, 2024

(54) PHOTOTHERAPY SYSTEM

(71) Applicant: Lumitex, Inc., Strongsville, OH (US)

(72) Inventors: Michael Kerns, Copley, OH (US); David G. Felty, Parma, OH (US); Peter Broer, Strongsville, OH (US)

(73) Assignee: Lumitex, Inc.

( * ) Notice: Subject to any disclaimer, the term of this patent is extended or adjusted under 35 U.S.C. 154(b) by 423 days.

(21) Appl. No.: 17/600,753

(22) PCT Filed: Apr. 3, 2020

(86) PCT No.: PCT/US2020/026607
§ 371 (c)(1),
(2) Date: Oct. 1, 2021

(87) PCT Pub. No.: WO2020/206275
PCT Pub. Date: Oct. 8, 2020

(65) Prior Publication Data
US 2022/0193444 A1    Jun. 23, 2022

Related U.S. Application Data

(60) Provisional application No. 62/828,828, filed on Apr. 3, 2019.

(51) Int. Cl.
*A61N 5/06* (2006.01)

(52) U.S. Cl.
CPC .... *A61N 5/0621* (2013.01); *A61N 2005/0626* (2013.01); *A61N 2005/063* (2013.01);
(Continued)

(58) Field of Classification Search
CPC .......... A61N 5/0621; A61N 2005/0626; A61N 2005/063; A61N 2005/0637; A61N 2005/0651
See application file for complete search history.

(56) References Cited

U.S. PATENT DOCUMENTS

2002/0138120 A1*  9/2002  Whitehurst ............ A61N 5/062
                                                          607/88
2006/0038192 A1    2/2006  Williams
(Continued)

FOREIGN PATENT DOCUMENTS

CN    108159574 A    6/2018
CN    109328091 A    2/2019
(Continued)

OTHER PUBLICATIONS

International Search Report for Application No. PCT/US2020/026607 dated Nov. 4, 2020.
(Continued)

*Primary Examiner* — Carl H Layno
*Assistant Examiner* — Aya Ziad Bakkar
(74) *Attorney, Agent, or Firm* — Renner, Otto, Boisselle & Sklar, LLP

(57) ABSTRACT

A phototherapy system having sensor(s) for detecting parameters associated with light generation by a light source and circuitry for modulating the light source based on the detected parameters. Also, a phototherapy system having a light guide interfacing with a light source at a connection point, an ambient light sensor, a connector light sensor for detecting (at the connection point) ambient light received by a light emitting pad that is directed into the light guide, and circuitry for determining whether the light guide is correctly connected to the light source based on a difference between the output of the ambient light source and the connector light sensor. Further, a phototherapy system including a light emitting pad having an identification tag and circuitry that modulates a light source based on the identification tag. Additionally, a phototherapy system including a casing encapsulating multiple light emitters and a light emitting pad.

23 Claims, 5 Drawing Sheets

(52) U.S. Cl.
CPC ............ *A61N 2005/0637* (2013.01); *A61N 2005/0651* (2013.01)

(56) References Cited

U.S. PATENT DOCUMENTS

| | | |
|---|---|---|
| 2010/0179469 A1 | 7/2010 | Hammond et al. |
| 2016/0287897 A1 | 10/2016 | Kaestle |
| 2016/0346564 A1 | 12/2016 | Burgmann |
| 2017/0080246 A1* | 3/2017 | Knight .................. A61G 10/02 |
| 2017/0080249 A1* | 3/2017 | Brawn ................. A61N 5/0603 |
| 2017/0312542 A1* | 11/2017 | Palaniswamy ............ A61F 7/08 |
| 2018/0243580 A1* | 8/2018 | Verhoeks ............... G16H 50/20 |
| 2019/0083809 A1* | 3/2019 | Zhang .................. A61N 5/0616 |
| 2019/0209861 A1 | 7/2019 | Dankers |

FOREIGN PATENT DOCUMENTS

| | | |
|---|---|---|
| EP | 0627243 A1 | 12/1994 |
| EP | 1147786 A2 | 10/2001 |
| WO | WO 01/14012 A1 | 3/2001 |
| WO | WO 2010/078581 A1 | 7/2010 |
| WO | WO 2015/075610 A1 | 5/2015 |
| WO | WO 2015/109393 A1 | 7/2015 |
| WO | WO 2017/220530 A1 | 12/2017 |

OTHER PUBLICATIONS

Chinese Office Action corresponding to counterpart Chinese patent application No. 202080035002.8 issued Nov. 28, 2023, English translation.

\* cited by examiner

PHOTOTHERAPY SYSTEM

RELATED APPLICATIONS

This application claims the benefit of U.S. 62/828,828 filed on Apr. 3, 2019, which is herein incorporated by reference in its entirety.

TECHNICAL FIELD

The present invention relates generally to a phototherapy device and system for delivering light to an infant's torso.

BACKGROUND

Phototherapy has long been used to treat newborn infants for various maladies including jaundice. Jaundice is caused by a buildup of bilirubin in the blood of infants. Exposing the infant's skin to certain types of light will quickly reduce the bilirubin to a safe level.

Blanket phototherapy for infants with jaundice is widely used in the developed world, with the advantage that it allows infant swaddling and mother/baby bonding during treatment. However, for reasons of economy, it is not widely available in the developing world.

SUMMARY

Jaundice is caused in most neonates and a certain percentage of full-term babies when the liver is inadequately developed to filter Bilirubin from the blood. Neonates and full-term babies with jaundice are commonly treated with blue light, which conjugates bilirubin molecules into lumirubin and photobilirubin, isomers of bilirubin which can be filtered by the kidneys.

In cost-sensitive environments typical in developing countries, babies are generally treated with overhead lights. A widely-acknowledged problem with this treatment mode is that the baby is typically left alone on its back with skin exposed under the lights. Commonly, its arms flail and panic often sets in, leaving the baby crying. When this happens, caregivers often disrupt or discontinue treatment to pick up and calm the baby.

Blanket phototherapy provides a desirable alternative, because it allows treatment to take place simultaneously with holding or swaddling the baby, leaving the baby calm as treatment continues without interruption. However, most effective blanket phototherapy tends to be expensive, limiting it to high-end hospitals in the developing world. Fiber optic construction used in the blanket phototherapy generally requires light from a high-power light-source in a remote box with complex electronics, a fan, and an intermediate fiber optic cable to keep heat away from babies, all-together making it too expensive a construction to deliver in cost-sensitive environments.

Lower-cost blanket phototherapy available today typically consists of a simple construction of individual, selectively-terminated fibers—an ineffective pad construction. This construction generally produces spots or points of light, which typically record readings less than the American Association of Pediatrics standard of 27 micro-watts per nanometer per centimeter squared, generally acknowledged globally to be the effective lower limit for infant phototherapy. Also, the system's optical inefficiency requires a high-powered light source (typically 100 watts or more) with sophisticated electronics and a cooling fan to dissipate the heat generated by the high power LED.

A more optically-efficient light transmission could lessen the optical power required at the source, allowing for a more cost-efficient construction. Similarly, a phototherapy system for home use that automates some of the calibration typically performed by technicians at hospitals would also allow for phototherapy use at home and/or at a lower cost.

The phototherapy system described herein includes novel features to decrease cost and increase effectiveness in a rugged environment. The phototherapy system has increased efficiency and effectiveness of optical delivery, enabling lower power, less complex and therefore less costly, and cooler light sources. The phototherapy system also includes a soft cover designed to minimize light attenuation to improve optical efficiency. The phototherapy system further includes a tracking device, allowing Durable Medical Equipment (DME) dealers to locate equipment easily, minimizing logistical cost.

The present invention provides a phototherapy system having one or more sensors for detecting parameters associated with light generation by a light source and circuitry for modulating the light source based on the detected parameters.

The present invention also provides a phototherapy system having a light guide interfacing with a light source at a connection point, an ambient light sensor, a connector light sensor for detecting (at the connection point) ambient light received by a light emitting pad that is directed into the light guide, and circuitry configured to determine whether the light guide is correctly connected to the light source based on a difference between the output of the ambient light source and the connector light sensor.

The present invention further provides a phototherapy system including a light emitting pad having an identification tag and circuitry that modulates generation of light by a light source based on calibration setting associated with the identification tag.

The present invention additionally provides a phototherapy system including a casing encapsulating a plurality of light emitters and a light emitting pad.

According to one aspect of the invention, there is provided phototherapy system including a light source, a light emitting pad, a sensor, and circuitry. The light emitting pad configured to emit light generated by the light source. The sensor detects a parameter of the light source. The sensor includes at least one of a photosensor, a thermal sensor, a voltage sensor, or a current sensor. When the sensor includes a photosensor, the photosensor receives a portion of the light generated by the light source. When the sensor includes a thermal sensor, the thermal sensor detects a temperature of the light source. When the sensor includes a voltage sensor, the voltage sensor detects a forward voltage of the light source. When the sensor includes a current sensor, the current sensor detects a current of the light source. The circuitry receives the detected parameter from the sensor and, based on the received parameters, issues a notification and/or modulates the light generated by the light source, such that electrical power to the light source is increased when the detected parameter is associated with a decrease in optical power of the light generated by the light source.

Alternatively or additionally, the circuitry is configured to modulate the light generated by the light source based on the detected parameter, such that optical power of the light emitted from the light emitting pad matches a predetermined optical power.

Alternatively or additionally, the phototherapy system also includes a housing. The sensor includes a plurality of thermal sensors. The light source and the plurality of thermal sensors are located in an internal cavity of the housing. The plurality of thermal sensors are located in different positions within the housing.

Alternatively or additionally, the circuitry also records the received parameters for different time points over a period of time and determines a rate of change of the recorded parameters during the period of time. When the determined rate of change is constant and non-zero across the period of time, the circuitry issues a first notification. When the determined rate of change includes a deviation where the rate of change increases or decreases by greater than a change threshold, the circuitry issues a second notification different from the first notification.

Alternatively or additionally, the phototherapy system may also include a heatsink thermally coupled to the light source and configured to transfer heat from the light source.

Alternatively or additionally, the sensor includes: an ambient temperature sensor configured to measure an ambient temperature of an environment in which the phototherapy system is located; and a light source temperature sensor configured to measure an operating temperature of the light source. The circuitry additionally determines a delta that is a difference between the measured ambient temperature and the measured operating temperature. The phototherapy system further includes a non-transitory computer readable medium configured to store historical deltas comprising the delta determined by the circuitry at different times. The circuitry also compares the delta determined at the current time to the historical deltas. When the delta determined at the current time deviates from the historical deltas, the circuitry issues a notification.

Alternatively or additionally, the heatsink is a thermoelectric cooler. The sensor includes: an ambient temperature sensor configured to measure an ambient temperature of an environment in which the phototherapy system is located; and a power sensor configured to measure an electric power utilized by the thermoelectric cooler to maintain a location of the light source at a set point temperature. The phototherapy system also includes a non-transitory computer readable memory storing a mapping of parameters indicating a range of normal power usage by the thermoelectric cooler for an ambient temperature. The circuitry also determines whether the measured electric power is within a range of normal power usage for the measured ambient temperature. When the measured electric power is not within the range of normal power usage, the circuitry issues a notification.

Alternatively or additionally, the notification issued is determined based on the measured electric power usage compared to electric power measurements of the thermoelectric cooler at previous times.

According to another aspect of the invention, there is provided a phototherapy system including a light source, a light guide, a light emitting pad, an ambient light source, a connector light source, circuitry, and a housing. The light guide is optically connected to the light emitting pad. The light guide is configured to interface with the light source at a connection point, such that light generated by the light source is received by the light guide and transmitted to the light emitting pad. The light emitting pad emits the light generated by the light source. The light source and the connector light sensor are located in an internal cavity of the housing. The ambient light sensor is configured to measure ambient light in an environment located outside the internal cavity of the housing. The light emitting pad is further configured to receive the ambient light and transfer the received ambient light to the light guide. The light guide is further configured to receive the ambient light from the light emitting pad and direct the light to the connection point. The connector light sensor measures the received ambient light at the connection point. The circuitry receives an ambient measurement from the ambient light sensor and receive a connector measurement from the connector light sensor. The circuitry also determines a difference between the ambient measurement and the connector measurement. When the determined difference is greater than an ambient light difference threshold, the circuitry issues a connection error notification.

According to a further aspect of the invention, there is provided phototherapy system including a light source, a light emitting pad, an identification tag, and circuitry. The identification tag outputs a signal identifying the light emitting pad. The circuitry modulates the generation of light by the light source and receive the identification signal from the identification tag. The circuitry also determines calibration settings of the light emitting pad based on the identification signal and modulates the generation of the light by the light source based on the determined calibration settings.

Alternatively or additionally, the calibration settings specify a light transmission efficiency of the light emitting pad and the circuitry determines the calibration settings based on a comparison of the light transmission efficiency of the light emitting pad to a standard light transmission efficiency value.

Alternatively or additionally, the phototherapy system also includes a motion sensor. The circuitry is configured to issue a notification when the motion sensor does not sense motion for a duration of time greater than a time threshold.

Alternatively or additionally, the phototherapy system may additionally include a first light guide, a second light guide, a first light sensor, and a second light sensor. The light source includes a first light emitter configured to transmit light to the light emitting pad via the first light guide and a second light emitter configured to transmit light to the light emitting pad via the second light guide. The first light sensor is configured to detect light received by the light emitting pad and transmitted to the first light guide by the light emitting pad. The second light sensor is configured to detect light received by the light emitting pad and transmitted to the second light guide by the light emitting pad. The circuitry alternates in time light emission by the first light emitter and the second light emitter and periodically records the light detected by the first light sensor and the light detected by the second light sensor. When the light detected by the first light sensor and the light detected by the second light sensor has not changed by a change threshold for a duration of time greater than a time threshold, the circuitry issues a no movement notification indicating that movement has not been detected.

Alternatively or additionally, the phototherapy system also includes a light guide configured to receive light from the light source and transfer the received light to the light emitting pad.

Alternatively or additionally, the phototherapy system further includes a ferrule configured to optically interface the light guide and the light source.

According to an additional aspect of the invention, there is provided a phototherapy system including a light source including a plurality of light emitters, a light emitting pad, and a casing. Each of the plurality of light emitters are configured to generate light. The light emitting pad is configured to emit the light generated by the light source. The casing encapsulates the light emitting pad and each of the light emitters.

Alternatively or additionally, the light source includes a plurality of light emitters. The plurality of light emitters interface with the light emitting pad along a lateral edge of the light emitting pad.

Alternatively or additionally, the phototherapy system also includes a stage considered to receive and support a rear surface or a side surface of the light emitting pad. The stage includes at least one of: a heat sink thermally coupled to the light source and configured to transfer heat from the light source or a power supply configured to supply power to the light source and the circuitry.

Alternatively or additionally, the power supply comprises an inductive charger.

Alternatively or additionally, the phototherapy system further includes a housing and a bed. The housing maintains the light source in an internal volume of the housing. The housing includes an aperture in an upward facing surface of the housing. The light source is positioned within the housing such that light generated by the light source is emitted through the aperture. The bed includes a depression for receiving the housing. The depression is shaped to receive the housing such that the upward facing surface of the housing is flush with a bedding surface of the bed. The housing includes retention features that do not protrude from the upward facing surface of the housing and that interface with complementary structures on the light emitting pad, such that light generated by the light source is received by the light emitting pad.

Alternatively or additionally, the phototherapy system includes a padding configured to be placed over the upward facing surface of the housing and at least a portion of the bedding surface of the bed when the light emitting pad is not optically connected to the light source.

Alternatively or additionally, the retention features include at least one of: a port for receiving a light guide optically connected to the light emitting pad or a magnetic connector configured to interface with a complementary magnetic connector on the light emitting pad, such that: when the magnetic connector engages with the complementary magnetic connector and the light source is emitting light, the light emitting pad receives light from the light source.

Alternatively or additionally, the light emitting pad includes identifier circuitry configured to transmit an identification of the light emitting pad to the circuitry, such that the circuitry receives the transmitted identification when the light emitting pad is optically connected to the light source and the circuitry prevents the light source from emitting light when the identification is not received indicating that a light emitting pad is not located optically connected to the light source.

Alternatively or additionally, the phototherapy system additionally includes a light guide, a ferrule, and a housing. The light guide configured to: interface at a connection point with the light source, receive light from the light source, and transfers the received light to the light emitting pad. The ferrule maintains an optical connection between the light guide and the light source at the connection point. The housing receives the light source in an internal volume of the housing. A portion of the ferrule extends outside of the housing and the extending portion of the ferrule is thermally connected to the light source, such that heat is transferred from the light source to outside of the housing by the ferrule via the extending portion of the ferrule.

Alternatively or additionally, the light source includes a plurality of light emitters.

Alternatively or additionally, the plurality of light emitters include a plurality of light emitting diodes (LEDs).

Alternatively or additionally, the phototherapy system does not include any moving parts.

Alternatively or additionally, the phototherapy system also includes a communication interface configured to communicate with an electronic device. The circuitry receives instructions from the electronic device via the communication interface. In response to the instructions, the circuitry causes the communication interface to provide the electronic device a record of the detected parameter over a period of time.

Alternatively or additionally, the circuitry is further configured to: receive from the electronic device via the communication interface a treatment schedule including a treatment start time and issue a notification at the start time.

Alternatively or additionally, the light emitting pad is a fiber optic panel formed from optical fiber.

Alternatively or additionally, optical fiber of the fiber optic panel includes a cladding and a light conducting core and light emission from the optical fiber is controlled by etching the cladding such that light is uniformly emitted by the light emitting pad.

Alternatively or additionally, the light emitting pad is a molded light guide not formed from optical fibers.

Alternatively or additionally, the light emitting pad has a top surface including a three-dimensionally contoured light emitting area.

Alternatively or additionally, the phototherapy system further includes a cover configured to receive the fiber optic panel within an internal volume of the cover, wherein the cover is made of layered spun fabric.

Alternatively or additionally, the phototherapy system additionally includes tracker circuitry configured to output a location of the phototherapy system.

Alternatively or additionally, the tracker circuitry is a global positioning system (GPS) tracking chip.

While a number of features are described herein with respect to embodiments of the invention; features described with respect to a given embodiment also may be employed in connection with other embodiments. The following description and the annexed drawings set forth certain illustrative embodiments of the invention. These embodiments are indicative, however, of but a few of the various ways in which the principles of the invention may be employed. Other objects, advantages and novel features according to aspects of the invention will become apparent from the following detailed description when considered in conjunction with the drawings.

BRIEF DESCRIPTION OF THE DRAWINGS

The annexed drawings, which are not necessarily to scale, show various aspects of the invention in which similar reference numerals are used to indicate the same or similar parts in the various views.

Figure 1:
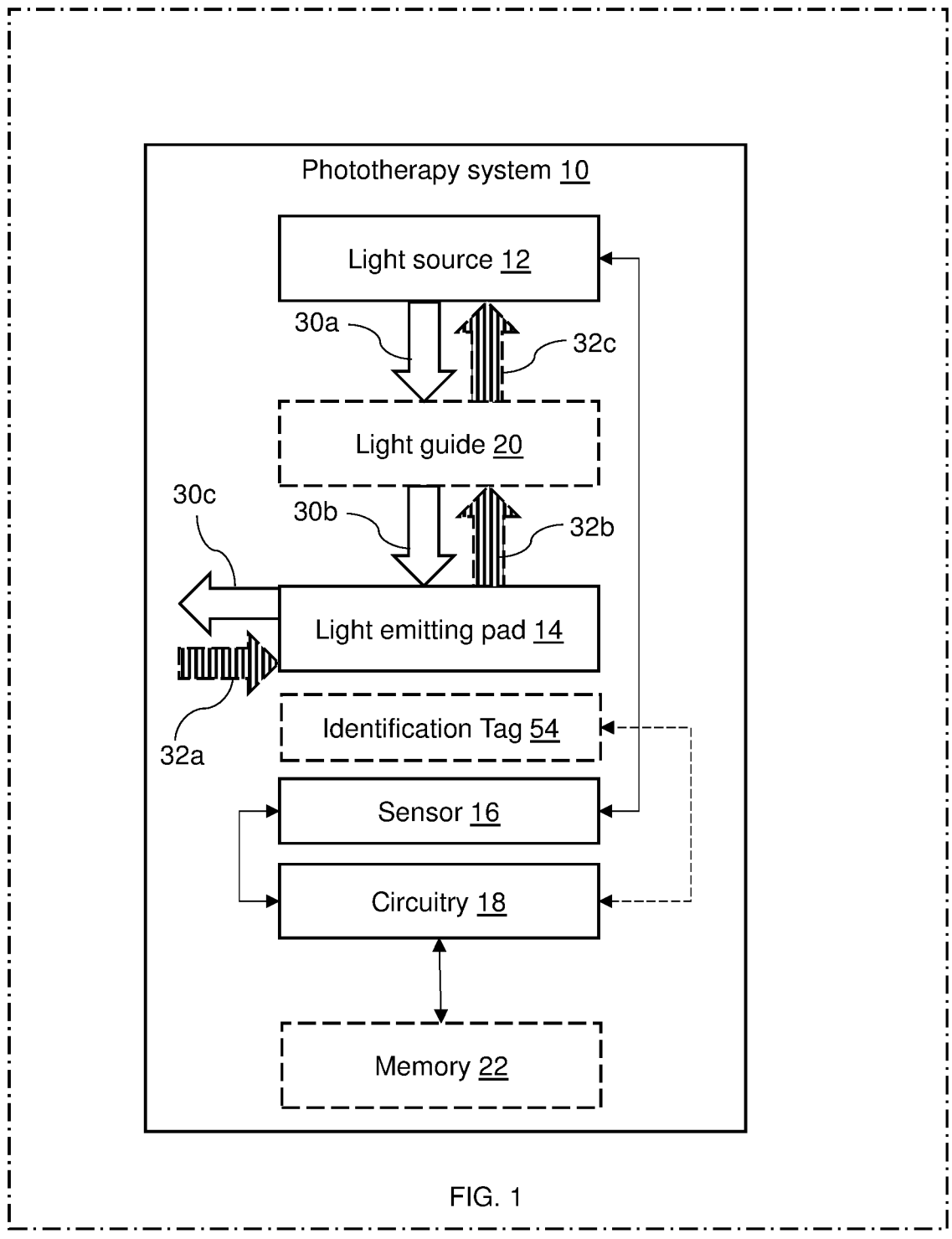
FIG. 1 is a block diagram of an embodiment of the phototherapy system showing transfer of light.

The present invention is described below in detail with reference to the drawings. In the drawings, each element with a reference number is similar to other elements with the same reference number independent of any letter designation following the reference number. In the text, a reference number with a specific letter designation following the reference number refers to the specific element with the number and letter designation and a reference number without a specific letter designation refers to all elements with the same reference number independent of any letter designation following the reference number in the drawings.

DETAILED DESCRIPTION

The present invention provides a phototherapy system having sensor(s) for detecting parameters associated with light generation by a light source. The output of the sensor(s) is received by circuitry and the circuitry modulates light generation by the light source based on the detected parameters.

The present invention also provides a phototherapy system having a light source, a light guide, a light emitting pad, an ambient light sensor, a connector light sensor, and circuitry. The light guide interfaces with the light source at a connection point. The ambient light sensor detects ambient light levels. Ambient light is received by the light emitting pad and transmitted from the light emitting pad to the light guide and from the light guide to the connection point. The connector light sensor detects light levels of the ambient light at the connection point (i.e., the ambient light that was received by the light emitting pad and transmitted via the light guide to the connection point). The circuitry determines whether the light guide is correctly connected to the light source based on a difference between the output of the ambient light source and the output of the connector light sensor.

The present invention further provides a phototherapy system including circuitry, a light source, and a light emitting pad having an identification tag. The circuitry receives an identification of the light emitting pad from the identification tag. The circuitry determines calibration settings for the light emitting pad based on the received identification. The circuitry then modulates generation of light by the light source based on the determined calibration settings.

The present invention additionally provides a phototherapy system including a casing encapsulating a plurality of light emitters and a light emitting pad.

Turning to FIG. 1, a phototherapy system 10 including a light source 12, a light emitting pad 14, a sensor 16, and circuitry 18 is shown. The light source 12 generates light 30 and the light emitting pad 14 emits the light 30 generated by the light source 12. The sensor 16 detects a parameter of the light source 12. Based on the detected parameter, the circuitry 18 either issues a notification or modulates the light generated by the light source.

The sensor 16 includes at least one of a photosensor, a thermal sensor, a voltage sensor, or a current sensor. When the sensor 16 includes a photosensor, the photosensor receives a portion of the light 30 generated by the light source 12. When the sensor 16 includes a thermal sensor, the thermal sensor detects a temperature of the light source 12. When the sensor 16 includes a voltage sensor, the voltage sensor detects a forward voltage of the light source 12. When the sensor includes a current sensor, the current sensor detects a current of the light source 16.

The sensor 16 may comprise one or more sensors of one or more types. For example, the sensor 16 may include an accelerometer, two thermal sensors, and two photosensors.

The circuitry 18 receives the detected parameter from the sensor 16 and issues a notification and/or controls the light source 12 based on the received parameters. For example, the circuitry 18 may modulate the light 30 generated by the light source 12 based on the detected parameter, such that optical power of the light 30 emitted from the light emitting pad 14 matches a predetermined optical power. As another example, when the received parameters indicate that the optical power of the light 30 generated by the light source 12 has decreased, the circuitry 18 may issue a notification indicating that service of the phototherapy system 10 is recommended.

The circuitry 18 may compare the parameter detected by the sensor 16 to an acceptable range for the detected parameter and, when the detected parameter is not within the accepted range, the circuitry 18 may modulate the light source 12, such that the optical power of the light generated by the light source is increased. As an example, the light 30 generated by the light source 12 may be modulated, such that electrical power to the light source 12 is increased when the detected parameter is associated with a decrease in optical power of the light 30 generated by the light source 12. After a duration of time, the circuitry 18 may receive an updated detected parameter from the sensor 16 and again compare the detected parameter to the acceptable range for the detected parameter. If the detected parameter is still outside of the accepted range, the circuitry 18 may again modulate the light source 12. In this way, the sensor 16 and circuitry 18 may act as a feedback loop to maintain the light source 12 operating within an acceptable range (e.g., an acceptable optical power).

As will be understood by one of ordinary skill in the art, the circuitry 18 may have various implementations. For example, the circuitry 18 may include any suitable device, such as a processor (e.g., CPU), programmable circuit, integrated circuit, memory and I/O circuits, an application specific integrated circuit, microcontroller, complex programmable logic device, other programmable circuits, or the like. The circuitry 18 may also include a non-transitory computer readable medium, such as random access memory (RAM), a read-only memory (ROM), an erasable programmable read-only memory (EPROM or Flash memory), or any other suitable medium. Instructions for performing the control of the light source 12 described herein may be stored in the non-transitory computer readable medium 22 and executed by the circuitry 18. The circuitry 18 may be communicatively coupled to the computer readable medium and network interface through a system bus, mother board, or using any other suitable structure known in the art.

Figure 2:
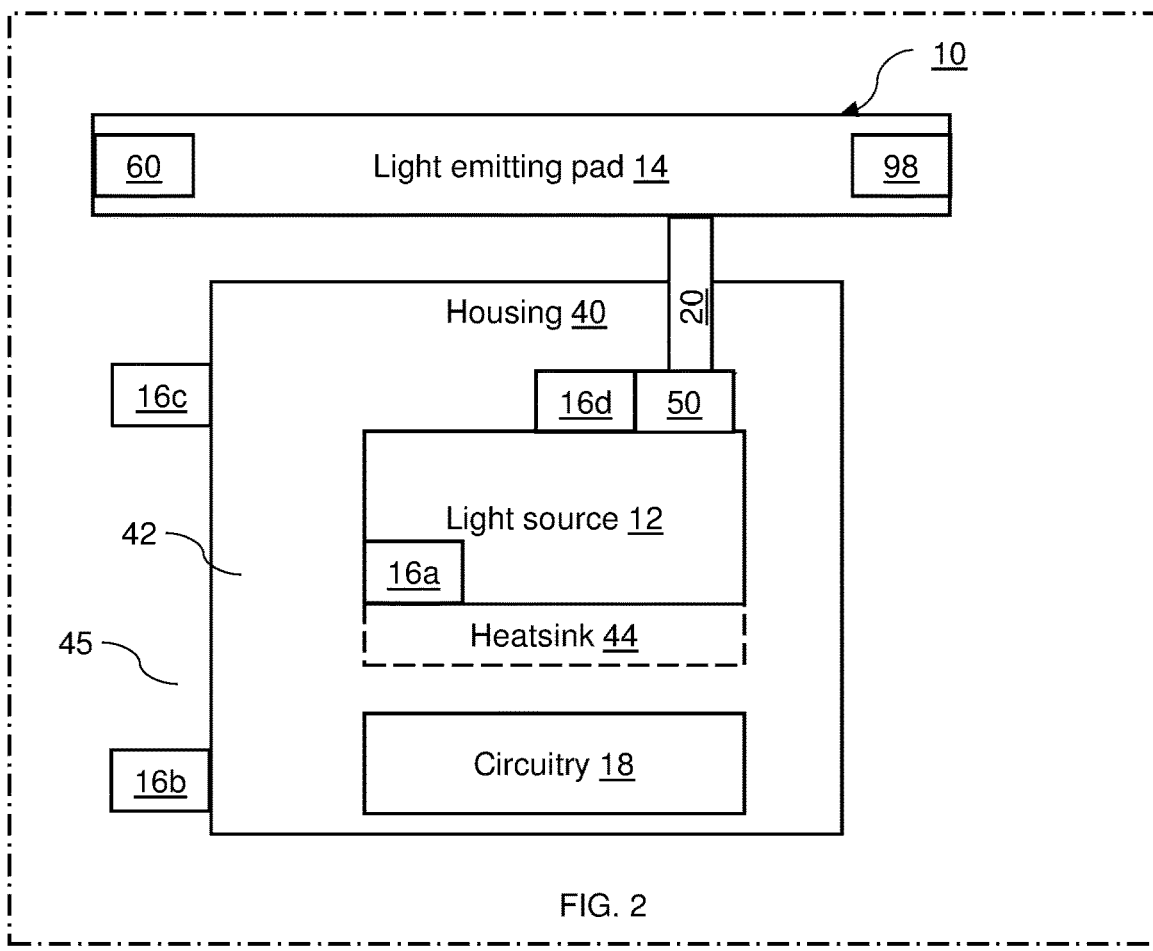
FIG. 2 is a schematic block diagram depicting physical connections between components of the phototherapy system.

Turning to FIG. 2, the phototherapy system may include a housing 40 and the sensor 16 may include a plurality of thermal sensors 16a, 16b. The light source 12 and the plurality of thermal sensors 16 may be located in an internal cavity 42 of the housing 40. The plurality of thermal sensors 16a, 16b may be located in different positions within the housing 40. As described above, when the parameters detected by the sensor 16 (i.e., the temperature at different positions), the circuitry 18 may compare the parameters to acceptable ranges for the parameters. For example, the acceptable ranges for the different temperature measurement locations may depend on other temperature measurements. That is, temperature readings away from the light source 12 may be used to determine an acceptable range for temperature measurements closer to the light source 12.

The circuitry 18 may record the parameters received from the sensor(s) at different time points over a period of time. The circuitry 18 may then determine a rate of change of the recorded parameters during the period of time. When the determined rate of change is constant and non-zero across the period of time, the circuitry 18 may issue a first notification. For example, the first notification may be a warning that maintenance of the phototherapy system 10 should be performed soon. When the determined rate of change includes a deviation where the rate of change increases or decreases by greater than a change threshold, the circuitry 18 may issue a second notification different from the first notification. For example, the second notification may be a warning that maintenance of the phototherapy system 10 should be performed immediately and that use of the phototherapy system 10 should not continue until maintenance has been performed. For example, when issuing the second notification, the circuitry 18 may also disable the light source until maintenance is performed.

For example, if the circuitry 18 determines a trend in detected parameters indicating a gradual decay in performance of the light source 12 (e.g., over many operating cycles), the circuitry 18 may determine that the light source 12 is losing efficiency due to aging. When this occurs, the circuitry 18 may issue a notification (also referred to as a warning) that the light source 18 should soon be replaced. The circuitry 18 may give a different notification when the efficiency of the light source 12 has been determined to be sufficient enough to possibly affect treatment.

Alternatively, if the circuitry 18 determines an abrupt change in performance, the circuitry 18 may signal an immediate warning (e.g., even if light output is maintained within a specified range), because the circuitry 18 may assume that some other process (e.g., other than aging of the components) has occurred. In this way, a portion of field service procedures currently performed can be automated and cost may be reduced by mitigating the risk that a service technician will blindly replace the light source 12 (a waisted cost if the light source is not faulty) when the real problem is caused by a different issue (e.g., a loose harness).

The light source 12 may be a single light emitter or a plurality of light emitters. For example, the light emitter(s) may be light emitting diode(s) (LED(s)), micro-LED(s), fluorescent source(s), incandescent source(s), laser(s), or any suitable source of light.

The light emitting pad 14 may each comprise any suitable structure for receiving light generated by the light source 12 and emitting the light from a light emission surface of the light emitting pad 14. For example, the light emitting pad light guide 20 may comprise woven optical fibers or clad flat fiber. The light emitting pad 14 may be formed of any suitable material.

Because a fiber optic light emitting pad 14 may be more efficient at delivering light due to the etching, the phototherapy system may require less power and cost in terms of the light source. For example, one or more low-power LED's can interface with one or more fiber optic bundles or ferrules, which channel light to the fiber optic panel. Because low-power LED's are less costly and produce less heat, electronic circuitry is simpler and cooling fans are unnecessary—factors contributing to cost efficiency. Design simplicity without moving parts also contributes to ruggedness, important in diverse environments such as rural hospitals or home use.

Additionally, typically fiber optic pads are enclosed in re-useable plastic covers, which in turn are enclosed in disposable soft spun-fabric, or paper, covers to protect babies' skin. These covers can attenuate brightness by 20% or more. However, in an embodiment of the current invention, a design of disposable covers minimizes light attenuation by a more efficient choice of, or layering of, materials. This contributes to system-efficiency, by reducing the brightness required from the LED to overcome the reduction in light caused by the fabric, or paper, cover.

Alternatively, light emitting pad may be configured to avoid using optical fiber. For example, the light emitting pad 14 may be a molded light guide not formed from optical fibers. As an example, the light emitting pad could instead be a light guide molded in flexible PMMA or silicone or even SLA printed. There are also opportunities for labor savings since you remove the loom/drum processes, as well as the hand layup and maybe even ferruling process for the pad builders. The light emitting pad 14 may have a top surface including a three-dimensionally contoured light emitting area. For example, the light emitting pad 14 may be a three-dimensionally (3D) contoured light emitting area (e.g., molded in flexible media or printed) that conforms better to the baby's body and illuminates more surface area of the skin at a given time.

In another embodiment, a 3d contoured light guide could improve surface area illumination and baby comfort, but the light guide may not be integrated to the pad. Instead, the light guide may be a separate mat-like piece that lays on top of a normal flat style pad. This piece could be offered in generic sizes like S, M, L. Or it could be offered in several styles to fit typical baby body types. As an example, a handheld optical scanner could be used in NICUs and DMEs that scans the baby's shape and makes a recommendation of which style of mat would fit best.

The phototherapy system may also include a cover that receives the fiber optic panel within an internal volume of the cover. The cover may be made of layered spun fabric.

The phototherapy system 10 may also include a heatsink 44 thermally coupled to the light source 12 to transfer heat from the light source 12. For example, the heatsink may comprise a mechanically stationary metal component thermally coupled to the light source 12 using thermal paste.

With continued reference to FIG. 2, the sensor 16 may include a light source temperature sensor 16a and an ambient temperature sensor 16b. The light source temperature sensor 16a may measure an operating temperature of the light source 12. The ambient temperature sensor 16b may measure an ambient temperature of an environment 45 in which the phototherapy system 10 is located. The circuitry 18 may determine a delta that is a difference between the measured ambient temperature and the measured operating temperature. Previously determined deltas may be stored as historical deltas in the non-transitory computer readable medium (also referred to as memory) 22. The circuitry 18 may compare the delta determined at the current time to the historical deltas retrieved from the memory 22. When the delta determined at the current time deviates from the historical deltas by greater than a delta threshold (e.g., 15%), the circuitry 18 may issue a notification. As described above, the notification may be a warning to perform maintenance in the future or the notification may be to perform maintenance immediately.

In an embodiment, the heatsink 44 may be a thermoelectric cooler and the sensor 16 may include an ambient temperature sensor 16*b* and a power sensor. As described above, the ambient temperature sensor 16*b* may measure an ambient temperature of the environment 45. The power sensor may measure an electric power utilized by the thermoelectric cooler to maintain a location of the light source at a set point temperature. The circuitry 18 may access from the memory 22 a mapping of parameters indicating a range of normal power usage by the thermoelectric cooler for maintaining the light source 12 at the setpoint temperature for a given ambient temperature. For example, the mapping of parameters may indicate previously recorded power utilization and ambient temperature combinations.

The circuitry 18 may determine whether the measured electric power is within a range of normal power usage for the measured ambient temperature based on the mapping of parameters stored in the memory. When the measured electric power is not within the range of normal power usage, the circuitry 18 may issue a notification. For example, the notification issued may be determined based on the measured electric power usage compared to electric power measurements of the thermoelectric cooler at previous times. That is, if the measured electric power usage for the ambient temperature is within a first notification range that is outside the range of normal power usage, then a first notification may be issued. Similarly, if the measured electric power usage for the ambient temperature is outside of the first notification range, but inside of a second notification range that encompasses the first notification range, then the circuitry 18 may issue a second notification.

Turning to FIGS. 1 and 2, in another embodiment, the phototherapy system 10 may include a light source 12, a light guide 20, a light emitting pad 14, sensors 16, and a housing 40. The sensors 16 may include an ambient light sensor 16*c* and a connector light sensor 16*d*. The light guide 20 is optically connected to the light emitting pad 14. The light guide 20 interfaces with the light source 12 at a connection point 50, such that the light 30 generated by the light source 12 is received by the light guide 20 and transmitted to the light emitting pad 14. The light source 12 and the connector light sensor 16*d* are located within an internal cavity 42 of the housing 40. The ambient light sensor 16*c* measures ambient light 32 in an environment 45 located outside the internal cavity 42 of the housing 40.

The connection point 50 may comprise a ferrule that optically interfaces the light guide 20 and the light source 12.

The light emitting pad 14 receives the ambient light 32 and transfers the received ambient light 32*a* to the light guide 20. The light guide 20 receives the ambient light 32*b* from the light emitting pad 14 and directs the light 32*c* to the connection point 50. The connector light sensor 16*d* measures the received ambient light 32*c* at the connection point 50.

The circuitry 18 receives an ambient measurement from the ambient light sensor 16*d* and a connector measurement from the connector light sensor 16*c*. The circuitry 18 determines a difference between the ambient measurement and the connector measurement. When the determined difference is greater than an ambient light difference threshold (indicating light loss during transfer from the light emitting pad 14 to the connection point 50, signaling an incorrect connection between the light guide 20 and the light source 12), the circuitry issues a connection error notification. The connection error notification may be a visual or audible notification that the light guide 20 is incorrectly connected to the light source 12. For example, the circuitry 18 may include a display that displays text and/or flashes to indicate that there is a connection error. Alternatively or additionally, the circuitry 18 may include a speaker that plays a sound (e.g., beeping) when there is a connection error.

The light guide 20 may each comprise any suitable structure for guiding light from a light source via total internal reflection. For example, the light guide 20 may comprise at least one of multi-stranded optical fibers, a single fiber solid core optical fiber, woven optical fibers, or clad flat fiber. The light guide 20 may be formed of any suitable material. For example, the light guide 20 may be made from at least one of glass or plastic.

In another embodiment, the phototherapy system 10 may include a light source 12, a light emitting pad 14, circuitry 18, and an identification tag 54. The identification tag 54 outputs a signal identifying the light emitting pad 14. The circuitry 18 receives the identification signal from the identification tag 54 and determines calibration settings of the light emitting pad 14 based on the identification signal. The circuitry 18 then modulates the generation of the light 30 by the light source 12 based on the determined calibration settings.

For example, the identification tag 54 may comprise an RFID tag and the circuitry 18 may receive a unique identifier as the identification signal from the identification tag 54. The circuitry 18 may look up the unique identifier in the memory to determine a calibration setting associated with the unique identifier. As another example, the identification signal may be the calibration settings for the light emitting pad 14.

The identification tag 54 may comprise any suitable device (e.g., a barcode, radio transmitter, etc.) for supplying information to the circuitry 18.

The calibration settings may specify a light transmission efficiency of the light emitting pad 14. The circuitry may determine the calibration settings based on a comparison of the light transmission efficiency of the light emitting pad 14 to a standard light transmission efficiency value. For example, the light transmission efficiency of the light emitting pad 14 may be 14% less than a standard light transmission efficiency value. The circuitry 18 may modulate the light source to compensate for the light transmission efficiency of the light pad by modulating the light source 12 such that the optical power of the light source 12 is increased by 14%.

Because phototherapy systems are frequently used with newborn infants, the phototherapy system may additionally issue a notification if motion is not sensed for a duration of time. For example, the phototherapy system 10 may include a motion sensor 60, such as an accelerometer and/or gyroscope. The circuitry 18 may issue a notification when the motion sensor 60 does not sense motion for a duration of time greater than a time threshold. For example, the circuitry 18 may issue an audible alarm when motion is not sensed by a preset time threshold (e.g., 30 seconds or 60 seconds).

Figure 3:
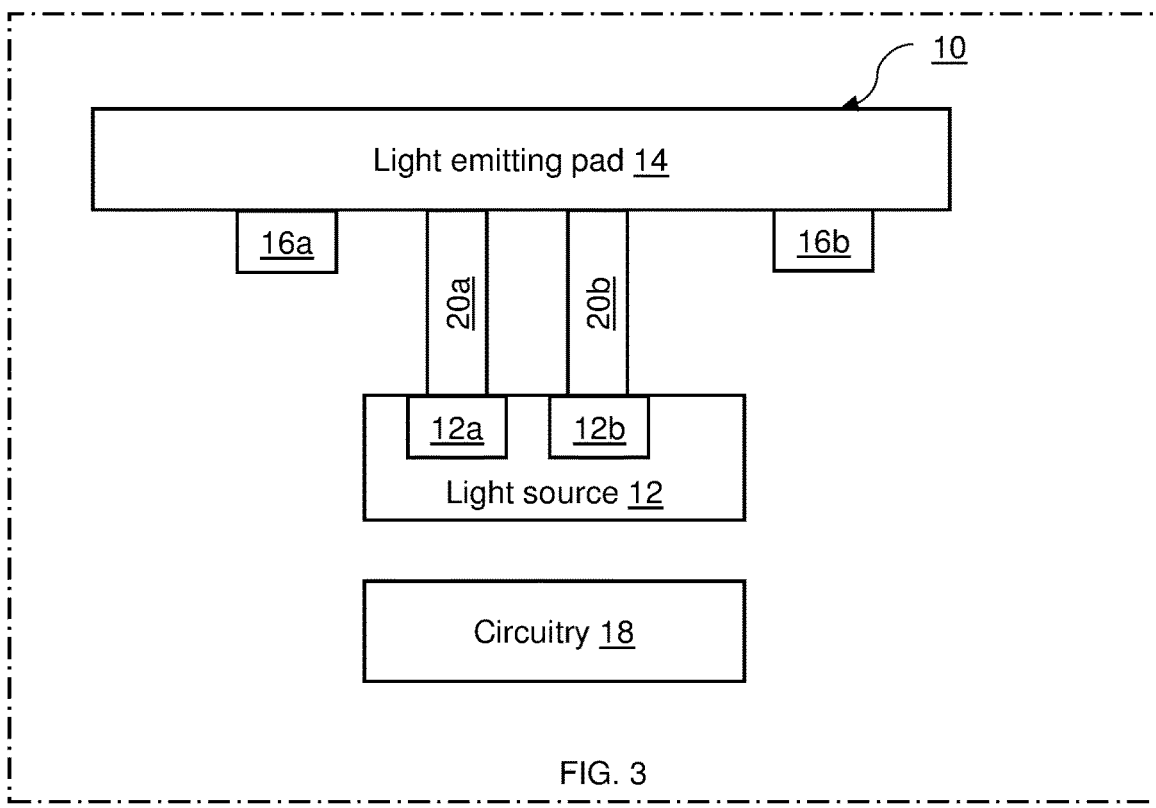
FIG. 3 is a schematic block diagram of a phototherapy system including two light guides.

Turning to the embodiment shown in FIG. 3, the phototherapy system 10 may include a light source 12, a light emitting pad 14, sensors 16, circuitry 18, and a light guide 20. The light guide 20 may include a first light guide 20*a* and a second light guide 20*b*. The sensor 16 may include a first light sensor 16*a* and a second light sensor 16*b*. The light source 12 may include a first light emitter 12*a* and a second light emitter 12*b*. The first light emitter 12*a* transmits light to the light emitting pad 14 via the first light guide 20*a*. The second light emitter 12*b* transmits light to the light emitting pad 14 via the second light guide 20*b*.

The first light sensor 16*a* detects light received by the light emitting pad 14 and transmitted to the first light guide 20*a* by the light emitting pad 14. For example, the first light sensor 16 detects a portion of the ambient light received by the light emitting pad 14 and a portion of the light generated by the second light emitter 12*b*. The second light sensor 16*b* detects light received by the light emitting pad 14 and transmitted to the second light guide 20*b* by the light emitting pad 14. For example, the second light source 16 detects a portion of the ambient light received by the light emitting pad 14 and a portion of the light generated by the first light emitter 12*a*.

The circuitry 18 alternates in time (e.g., the light emitters do not emit light at the same time) light emission by the first light emitter 12*a* and the second light emitter 12*b*. The circuitry 18 also periodically (e.g., every 100 milliseconds) records the light detected by the first light sensor 16*a* and the light detected by the second light sensor 16*b*. When the light detected by the first light sensor 16*a* and the light detected by the second light sensor 16*b* have not changed by a change threshold for a duration of time greater than a time threshold, the circuitry may issue a no movement notification indicating that movement has not been detected. For example, the circuitry 18 may determine a difference values output by the first light sensor 16*a* and the second light sensor 16*b* and when this difference is not greater than 10% for any two images in the last 60 seconds, the circuitry 18 may issue the no movement notification.

Figure 4:
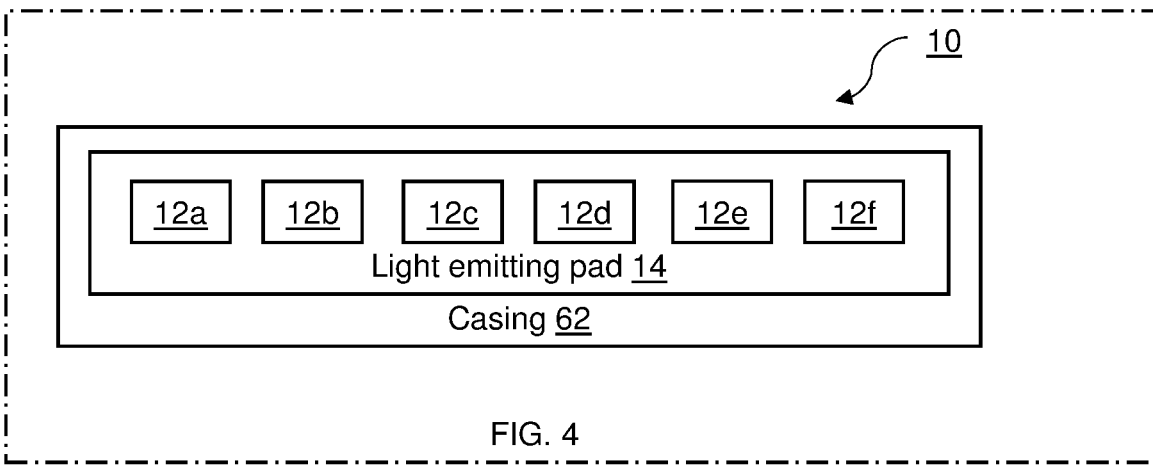
FIG. 4 is a schematic block diagram of a phototherapy system including a casing.

Turning to FIG. 4, an embodiment of the phototherapy system 10 is shown including a light source 12, a light emitting pad 14, and a casing 62. The light source 12 includes a plurality of light emitters 12*a*-12*f*. Each of the plurality of light emitters 12 are configured to generate light. The light emitting pad 14 emits the light generated by the light source 12. The casing 62 encapsulates the light emitting pad 14 and each of the light emitters 12.

For example, instead of using a light source 12 located separately from the light emitting pad 14, the light source 12 may instead be integrated into the light emitting pad 14 itself. That is, the light emitting pad may be formed from a gel with light emitters embedded in the gel. For example, a clad flat fiber including multiple light emitters (e.g., LEDs) may be encased in a gel (e.g., polyurethane). Electrical connection may be made to the light emitters at an edge of the gel. In an alternative embodiment, the light emitters may be micro-LEDs (without a separate light guide) embedded in the gel. Similarly, electrical connection to provide power to the micro-LEDs may be made at a surface of the light emitting pad.

Figure 5:
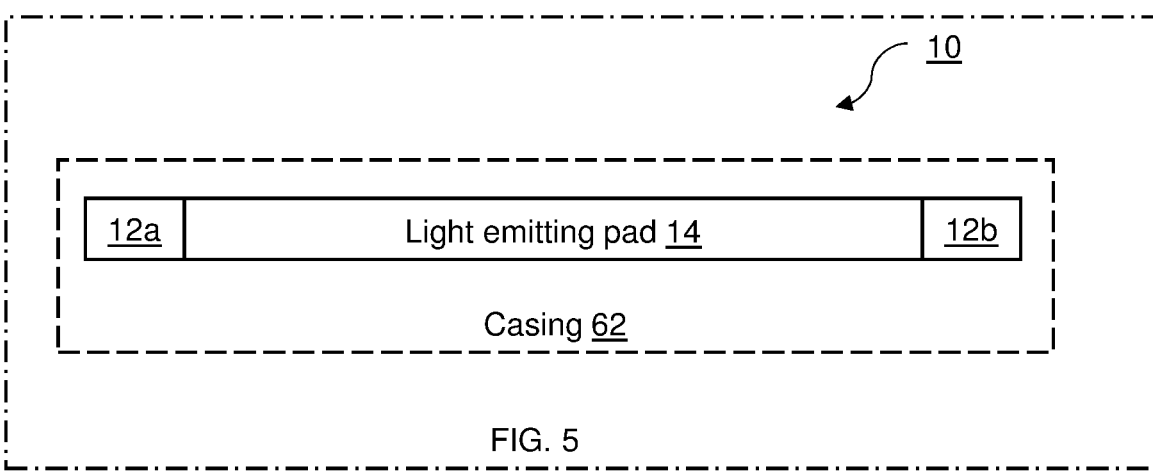
FIG. 5 is a schematic block diagram of a phototherapy system including a light emitting pad that is illuminated by a light source along a lateral edge.

As shown in FIG. 5, an embodiment of the phototherapy system 10 is shown including a plurality of light emitters 12 that interface with the light emitting pad 14 along a lateral edge 64 of the light emitting pad 14.

As an example, the light source 12 may be a traditional fiber insert and a strip of small LEDs aligned along one edge of the insert. With a series of small LEDs, light is well distributed and a rudimentary style of coupling optic may be used (e.g., a molded acrylic strip with a series of indents on one side to receive the LEDs and on the other side a cavity to receive the ends of optical fibers forming the light emitting pad). The fiber ends could be clear UV-cure epoxied in place to a uniform light coupling.

By eliminating the optical cabling and the need for a single large collimating reflector, significant gains in optical efficiency may be achieved, translating to significantly lower thermal waste. Waste heat could also be routed through a plastic cover of the pad by doping it with a thermally conductive additive and let it dissipate to ambient or even be used to warm the baby.

Figure 6:
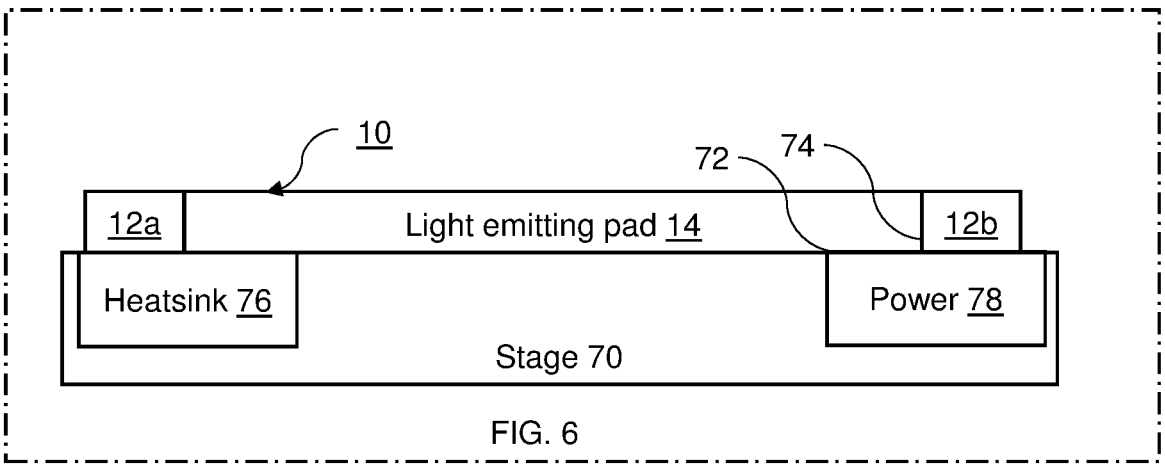
FIG. 6 is a schematic block diagram of a phototherapy system including a stage.

Turning to FIG. 6, an embodiment of the phototherapy system 10 may additionally include a stage 70 that receives and support a rear surface 72 or a side surface 74 of the light emitting pad 14. The stage 70 includes at least one of a heat sink 76 or a power supply 78. The heat sink 76 is thermally coupled to the light source 14 and configured to transfer heat from the light source 12. The power supply 76 supplies power to the light source 12 and the circuitry 18. For example, the power supply 76 may be an inductive charger. The power supply 76 may be any suitable device (e.g., a connector to a wall wort) for supplying power to the light source 12.

Figure 7:
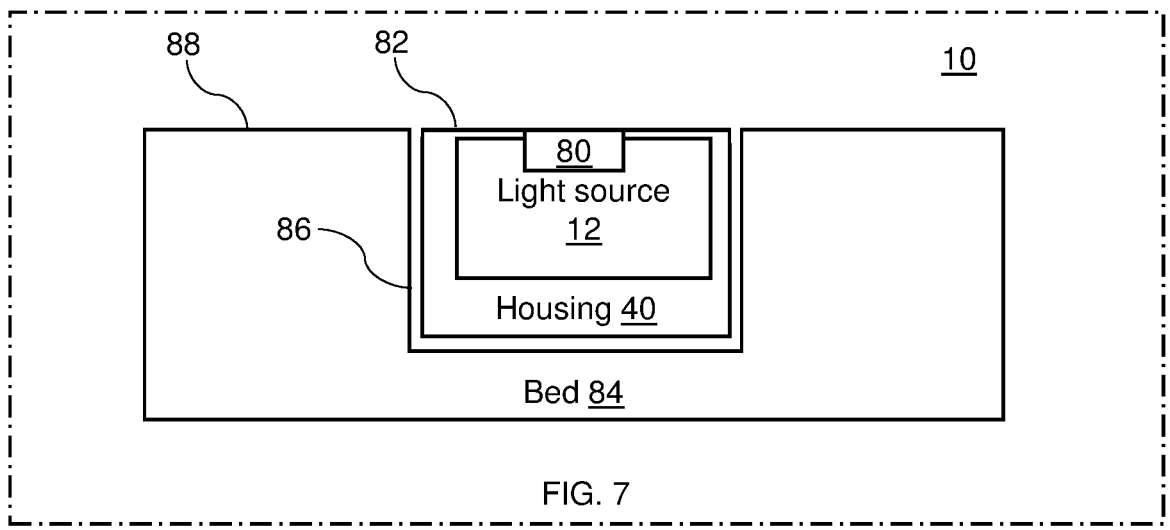
FIG. 7 is a schematic block diagram of a phototherapy system including a bed.

Turning to FIG. 7, a phototherapy system 10 including a light source 12, a housing 40, and a bed 84 is shown. The housing 40 maintains the light source 12 in an internal volume 42 of the housing 40. The housing 40 includes an aperture 80 in an upward facing surface 82 of the housing 40. The light source 12 is positioned within the housing 40 such that light generated by the light source 12 is emitted through the aperture 80. The bed 84 includes a depression 86 for receiving the housing 40. The depression 86 is shaped to receive the housing 40 such that the upward facing surface 82 of the housing 40 is flush with a bedding surface 88 of the bed 84. In this way, when the light emitting pad 14 is laid over the bedding surface 88 and the housing 40, the light emitting pad 14 lays flat and receives light from the light source 12.

Figure 8:
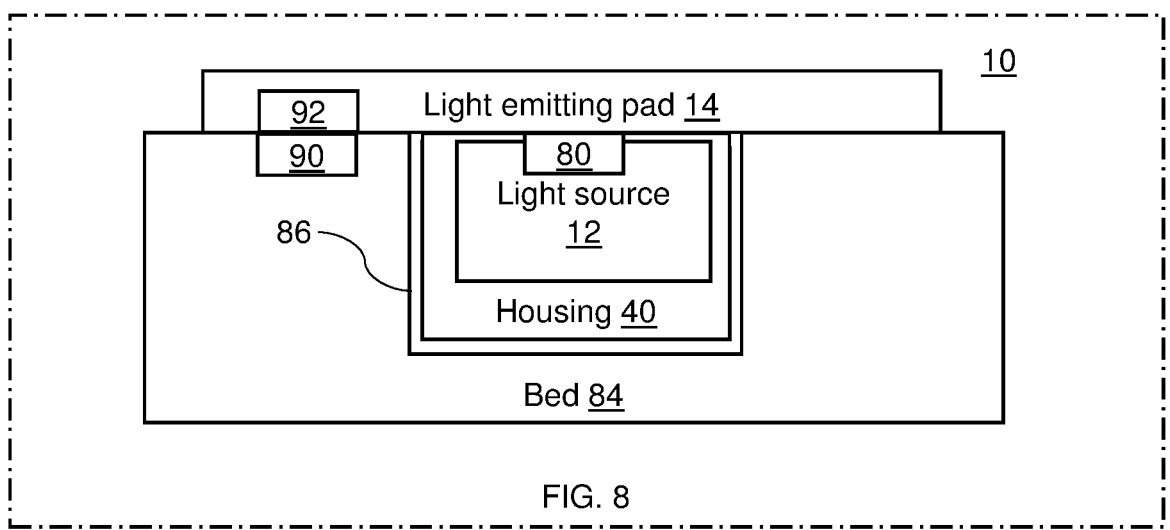
FIG. 8 is a schematic block diagram of the phototherapy system of FIG. 7 additionally including a light emitting pad.
Figure 9:
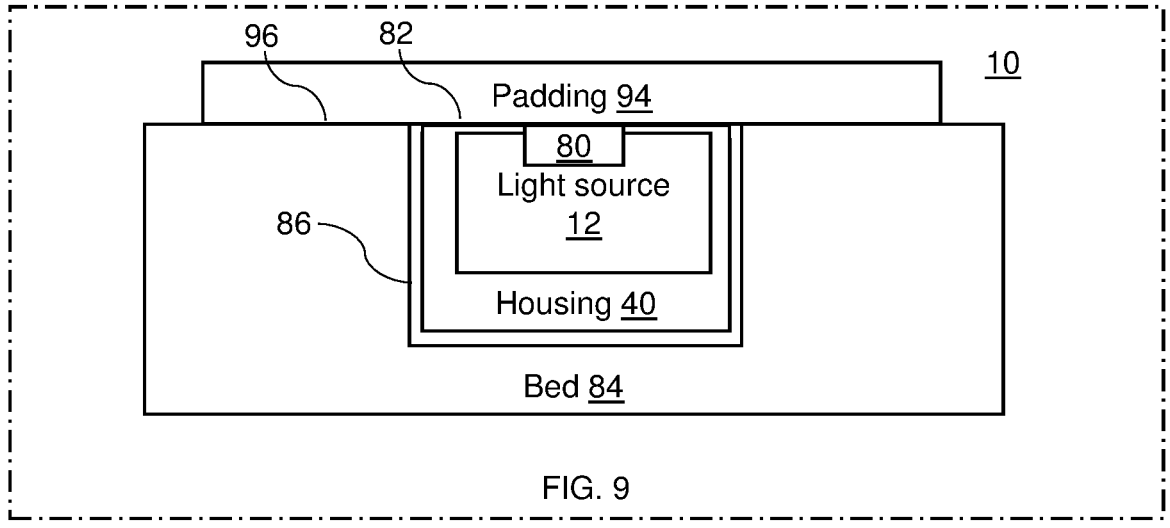
FIG. 9 is a schematic block diagram of the phototherapy system of FIG. 7 further including a padding.

Turning to FIG. 8, the phototherapy system 10 of FIG. 7 is shown including a light emitting pad 14. The housing 40 includes retention features 90 that do not protrude from the upward facing surface 82 of the housing 40. The retention features 90 interface with complementary structures 92 on the light emitting pad 14, such that light generated by the light source 12 is received by the light emitting pad 14. For example, by not protruding, the retention features reduce the chance of accumulating dirt or snagging fabric.

The retention features 90 may be a port for receiving a light guide 20 optically connected to the light emitting pad 14 or a magnetic connector that interfaces with a complementary magnetic connector on the light emitting pad 14, such that, when the magnetic connector engages with the complementary magnetic connector and the light source 12 is emitting light, the light emitting pad 14 receives light from the light source 12.

Figure 10:
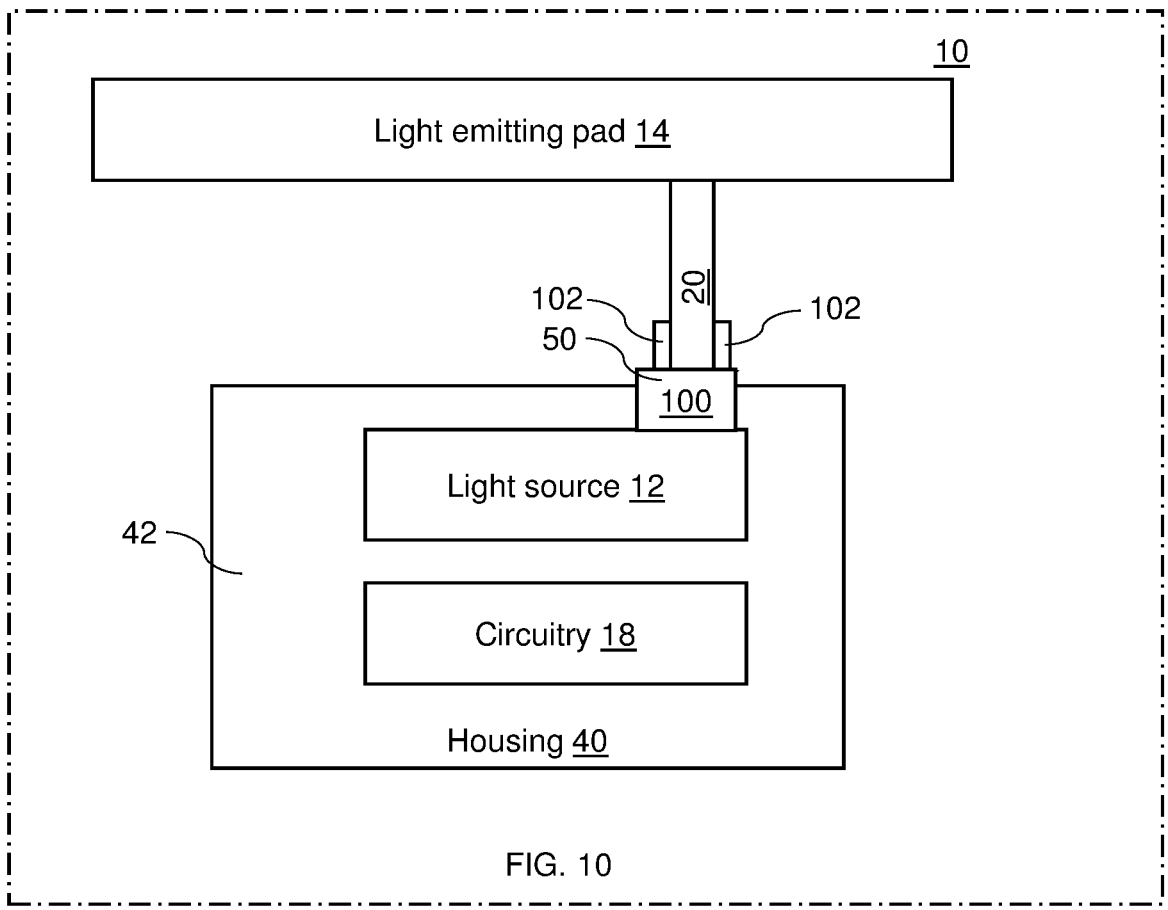
FIG. 10 is a schematic block diagram of a phototherapy system including a light guide, a housing, and a ferrule.

As shown in FIG. 10, the phototherapy system 10 may also include a padding 94 that is placed over the upward facing 82 surface of the housing 40 and at least a portion of the bedding surface 96 of the bed 84 when the light emitting pad 14 is not optically connected to the light source 12. In this way, only the light emitting pad 14 needs to be removed and padding 94 laid down for the bed 84 to be used as a sleeping surface.

Turning back to FIG. 2, the light emitting pad 14 may include identifier circuitry 98 configured to transmit an identification of the light emitting pad 14 to the circuitry 18, such that the circuitry 18 receives the transmitted identification when the light emitting pad 14 is optically connected to the light source 12 and the circuitry 18 prevents the light source 12 from emitting light when the identification is not received (indicating that a light emitting pad 14 is not optically connected to the light source). In this way, the phototherapy system 10 may prevent the light source 12 from generating light when a light emitting pad 14 is not connected correctly. That is, if the light emitting pad 14 is incorrectly connected (e.g., such that only a portion of the light generated by the light source 12 is being emitted from the light emitting pad 14), the light source 12 may be prevented from emitting light so that a patient does not receive an incorrect (in this example too low) optical dose.

Turning to FIG. 10, the phototherapy system 10 may include a light guide 20, a housing 40, and a ferrule 100. The light guide interfaces at a connection point 50 with the light source 12. The light guide 20 receives light from the light source 12 and transfers the received light to the light emitting pad 14. The ferrule 100 maintains an optical connection between the light guide 20 and the light source 12 at the connection point 50. The housing 40 receives the light source 12 in an internal volume 42 of the housing 40. A portion 102 of the ferrule 100 extends outside of the housing 40 and the extending portion 102 of the ferrule is thermally connected to the light source 12, such that heat is transferred from the light source 12 to outside of the housing 40 by the ferrule 100 via the extending portion 102 of the ferrule.

For example, the extending portion 102 of the ferrule may be a brass portion of the ferrule that extends out past a plastic housing 40. In this way, heat from the light source may be transferred by the extending portion 102 of the ferrule outside of the housing 40.

By using such heat transfer mechanism, it is possible for the phototherapy system 10 to not include any moving parts (e.g., no fans for heat exchange). The lack of moving parts may reduce required maintenance and reduce failure of the device, improving performance of the device.

Figure 11:
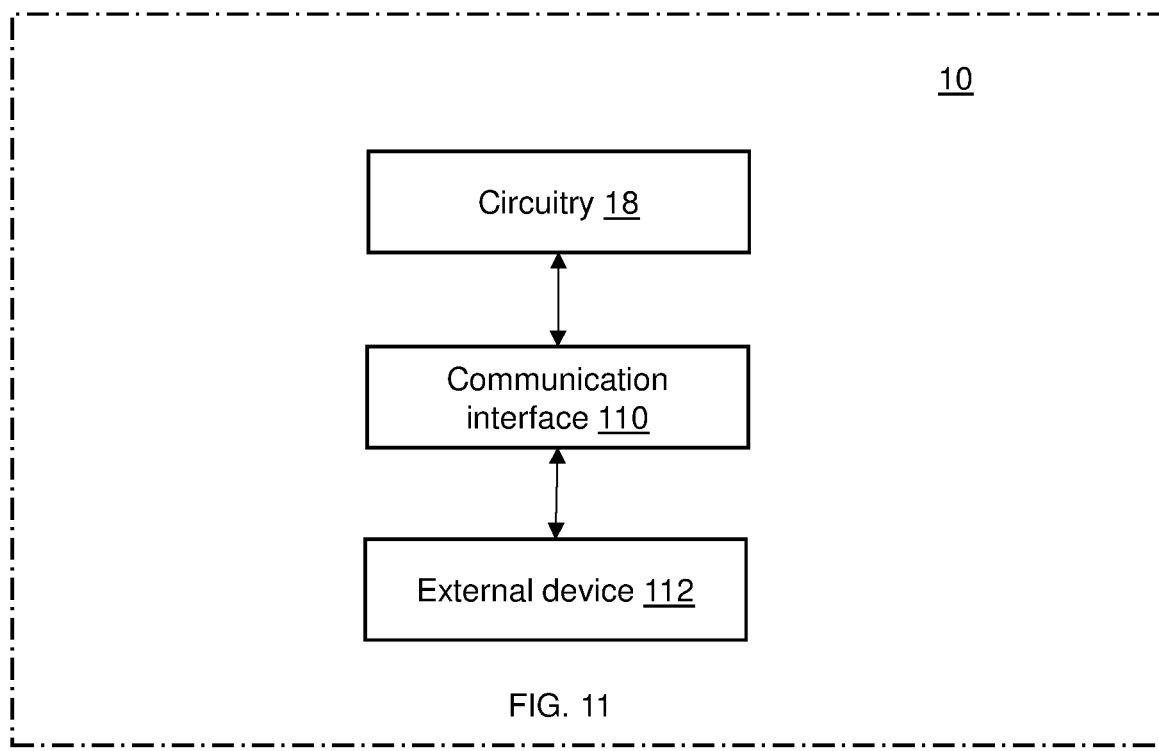
FIG. 11 is a block diagram of a phototherapy system including a communication interface.

As shown in FIG. 11, the phototherapy system 10 may include a communication interface 110 to communicate with an electronic device 112. The circuitry 18 may receive instructions from the electronic device 112 via the communication interface 110. In response to the instructions, the circuitry 18 may cause the communication interface 110 to provide the electronic device 112 a record of the parameter detected by the sensor(s) 16 over a period of time.

The circuitry 18 may also receive from the electronic device 114 via the communication interface 110 a treatment schedule including a treatment start time. The circuitry 18 may issue a notification at the start time. That is, the phototherapy system 10 may improve performance of phototherapy by alerting users when it is time to begin scheduled phototherapy.

For example, a service technician could use the communication interface 110 to establish an interface with an application (also referred to as an app) running on an external device 112 (e.g., a smart phone). In this example, the application may interface with the phototherapy system over a Bluetooth or WIFI connection to display performance of the light source over time (e.g., previously detected parameters by the sensor(s) 16), as well as allow the service technician to reference live help in the form of diagnostics guidance (e.g., if problem is X→check Y and Z), installation videos for FRU (Field Replaceable Units) components, online forms for post-maintenance checkout data, a feature that builds a shopping cart to support typical maintenance procedures and then places component orders, notification of preventative maintenance intervals, black box data (so if the unit is to be sent for RMA (Return Material Authoriza-tion), choose this function to dump data from the last X hours of operation to be sent to a given server), entering a patient's treatment schedule info (e.g., could be used for pushing reminders to the home care user of treatment frequency and time or, at prescribed times of the day, the system could automatically start and load the treatment time and sound a notification waiting for the parent to hit the button and start treatment).

The communication interface 110 may comprise a wireless network adaptor, an Ethernet network card, or any suitable device that provides an interface between the communication interface 110 and an external device 112. The communication interface 110 may be communicatively coupled to the computer readable medium 22, such that the communication interface 110 is able to send data stored on the computer readable medium 22 across the network and store received data on the computer readable medium 22. The communication interface 110 may also be communicatively coupled to the circuitry 18 such that the circuitry is able to control operation of the communication interface 110. The communication interface 110, computer readable medium 22, and circuitry 18 may be communicatively coupled through a system bus, mother board, or using any other suitable manner as will be understood by one of ordinary skill in the art.

The light emitting pad 14 may be a fiber optic panel formed from optical fiber. For example, the optical fiber of the optical fiber panel may include a cladding and a light conducting core. Light emission from the optical fiber may be controlled by etching the cladding such that light is uniformly emitted by the light emitting pad. Etching of the optical fiber may be economically achieved with industrial means available today.

The phototherapy system may also include tracker circuitry 120 that outputs (e.g., to circuitry 18) a location of the phototherapy system 10. The tracker circuitry 120 may be a global positioning system (GPS) tracking chip. That is, the tracker circuitry 120 may using GPS to determine a location of the phototherapy system 10.

The tracker circuitry 120 addresses a frequent problem with phototherapy in cost-sensitive environments (particularly when delivered in the home): the ability for an equipment supplier (typically a DME) to recover equipment after use.

The above described embodiments of the phototherapy system may be combined together in any suitable combination. For example, features from different embodiments separately described herein may be combined together to form different combinations. The features described in the different embodiments enable a cost-efficient phototherapy system that can extend the advantages of blanket phototherapy to families in cost-sensitive environments around the world.

All ranges and ratio limits disclosed in the specification and claims may be combined in any manner. Unless specifically stated otherwise, references to "a," "an," and/or "the" may include one or more than one, and that reference to an item in the singular may also include the item in the plural.

Although the invention has been shown and described with respect to a certain embodiment or embodiments, equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

The invention claimed is:

1. A phototherapy system comprising:
a light source;
a light emitting pad configured to emit light generated by the light source;
an identification tag configured to output a signal identifying the light emitting pad; and
circuitry configured to:
modulate the generation of light by the light source;
receive the identification signal from the identification tag;
determine calibration settings of the light emitting pad based on the identification signal, wherein:
the calibration settings specify a light transmission efficiency of the light emitting pad; and
the circuitry determines the calibration settings based on a comparison of the light transmission efficiency of the light emitting pad to a standard light transmission efficiency value; and
modulate the generation of the light by the light source based on the determined calibration settings.

2. The phototherapy system of claim 1, further comprising:
a sensor for detecting a parameter of the light source, wherein:
the sensor includes at least one of a photosensor, a thermal sensor, a voltage sensor, or a current sensor;
when the sensor includes a photosensor, the photosensor receives a portion of the light generated by the light source;
when the sensor includes a thermal sensor, the thermal sensor detects a temperature of the light source;
when the sensor includes a voltage sensor, the voltage sensor detects a forward voltage of the light source; and
when the sensor includes a current sensor, the current sensor detects a current of the light source;
wherein the circuitry is further configured to:
receive the detected parameter from the sensor; and
record the received parameters for different time points over a period of time;
determine a rate of change of the recorded parameters during the period of time;
when the determined rate of change is constant and non-zero across the period of time, issue a first notification; and
when the determined rate of change includes a deviation where the rate of change increases or decreases by greater than a change threshold, issue a second notification different from the first notification.

3. The phototherapy system of claim 2, wherein the circuitry is configured to modulate the light generated by the light source based on the detected parameter, such that optical power of the light emitted from the light emitting pad matches a predetermined optical power.

4. The phototherapy system of claim 2, further comprising a housing, wherein:
the sensor includes a plurality of thermal sensors;
the light source and the plurality of thermal sensors are located in an internal cavity of the housing; and
the plurality of thermal sensors are located in different positions within the housing.

5. The phototherapy system of claim 2, further comprising a heatsink thermally coupled to the light source and configured to transfer heat from the light source:
wherein the sensor includes:
an ambient temperature sensor configured to measure an ambient temperature of an environment in which the phototherapy system is located; and
a light source temperature sensor configured to measure an operating temperature of the light source;
wherein the circuitry is further configured to:
determine a delta comprising a difference between the measured ambient temperature and the measured operating temperature;
further comprising a non-transitory computer readable medium configured to store historical deltas comprising the delta determined by the circuitry at different times;
wherein the circuitry is additionally configured to:
compare the delta determined at the current time to the historical deltas;
when the delta determined at the current time deviates from the historical deltas, issue a notification.

6. The phototherapy system of claim 5:
wherein the heatsink comprises a thermoelectric cooler;
wherein the sensor includes:
an ambient temperature sensor configured to measure an ambient temperature of an environment in which the phototherapy system is located; and
a power sensor configured to measure an electric power utilized by the thermoelectric cooler to maintain a location of the light source at a set point temperature;
further comprising a non-transitory computer readable memory storing a mapping of parameters indicating a range of normal power usage by the thermoelectric cooler for an ambient temperature, wherein:
the circuitry is further configured to:
determine whether the measured electric power is within a range of normal power usage for the measured ambient temperature; and
when the measured electric power is not within the range of normal power usage, issue a notification.

7. The phototherapy system of claim 6, wherein the notification issued is determined based on the measured electric power usage compared to electric power measurements of the thermoelectric cooler at previous times.

8. The phototherapy system of claim 1, further comprising a motion sensor, wherein the circuitry is configured to issue a notification when the motion sensor does not sense motion for a duration of time greater than a time threshold.

9. The phototherapy system of claim 1, further comprising a light guide configured to receive light from the light source and transfer the received light to the light emitting pad.

10. The phototherapy system of claim 9, further comprising a ferrule configured to optically interface the light guide and the light source.

11. The phototherapy system of claim 10, wherein:
the light source includes a plurality of light emitters, wherein each of the plurality of light emitters are configured to generate light; and a casing configured to encapsulate the light emitting pad and each of the light emitters.

12. The phototherapy system of claim 11, wherein the plurality of light emitters interface with the light emitting pad along a lateral edge of the light emitting pad.

13. The phototherapy system of claim 1, further comprising a stage considered to receive and support a rear surface or a side surface of the light emitting pad, wherein the stage includes at least one of:
a heat sink thermally coupled to the light source and configured to transfer heat from the light source; or
a power supply configured to supply power to the light source and the circuitry.

14. The phototherapy system of claim 1, further comprising a stage configured to receive and support a rear surface a side surface of the light emitting pad, wherein the stage includes an inductive charger power supply configured to supply power to the light source and the circuitry.

15. The phototherapy system of claim 1, wherein the light emitting pad includes identifier circuitry configured to transmit an identification of the light emitting pad to the circuitry, such that the circuitry receives the transmitted identification when the light emitting pad is optically connected to the light source and the circuitry prevents the light source from emitting light when the identification is not received indicating that a light emitting pad is not located optically connected to the light source.

16. The phototherapy system of claim 1, wherein the phototherapy system does not include any moving parts.

17. The phototherapy system of claim 1, further comprising a communication interface configured to communicate with an electronic device, wherein:
the circuitry receives instructions from the electronic device via the communication interface; and
in response to the instructions, the circuitry causes the communication interface to provide the electronic device a record of a detected parameter over a period of time.

18. The phototherapy system of claim 1, wherein the circuitry is further configured to:
receive from the electronic device via the communication interface a treatment schedule including a treatment start time; and
issue a notification at the start time.

19. The phototherapy system of claim 1, wherein the light emitting pad is a fiber optic panel formed from optical fiber including a cladding and a light conducting core and light emission from the optical fiber is controlled by etching the cladding such that light is uniformly emitted by the light emitting pad.

20. The phototherapy system of claim 1, wherein the light emitting pad is a molded light guide not formed from optical fibers.

21. The phototherapy system of claim 1, wherein the light emitting pad has a top surface including a three-dimensionally contoured light emitting area.

22. The phototherapy system of claim 1, further comprising a cover configured to receive a fiber optic panel within an internal volume of the cover, wherein the cover is made of layered spun fabric.

23. The phototherapy system of claim 1, further comprising tracker circuitry configured to output a location of the phototherapy system.

* * * * *